United States

Williams

[11] 4,122,271
[45] Oct. 24, 1978

[54] PIPERAZINYL-N,N'-BIS(DITHIOTINCAR-BAMATES)

[75] Inventor: John Wesley Williams, Waukegan, Ill.

[73] Assignee: Abbott Laboratories, North Chicago, Ill.

[21] Appl. No.: 772,184

[22] Filed: Mar. 14, 1977

[51] Int. Cl.$^2$ .................. C07D 295/18; A61K 31/495
[52] U.S. Cl. ........................................ 544/225; 71/66; 71/67; 106/15 R; 424/250

[58] Field of Search ..................................... 260/250 R

*Primary Examiner*—Jose Tovar
*Attorney, Agent, or Firm*—Paul D. Burgauer; Robert L. Niblack

[57] ABSTRACT

Protection against certain aquatic pests can be obtained by use of certain alkyl tin dithiocarbamates in the coating for materials exposed to such pests or the aquatic enivornment in contact with these materials.

3 Claims, No Drawings

PIPERAZINYL-N,N'-BIS(DITHIOTINCARBAMATES)

DETAILED DESCRIPTION OF THE INVENTION

Algae, spores, bacteria and barnacles are aquatic pests that are the cause of deterioration for many man-made structures exposed to water. Some of these pests exist in fresh water as well as in salt water and they often grow and thrive in industrial waters, e.g., cooling liquids, storage tanks etc. In either case, they deface the surfaces of materials in contact with such waters. Unfortunately, these pests also attack painted surfaces with the result that boats, ships, docks and piers look unsightly soon after the body of water comes into steady contact with the surface of the painted or unpainted structure.

It has now been found that structures exposed to bodies of water are protected from attack by algae, barnacles, spores or bacteria by adding to said body of water or to the surface coating of said structures in contact with such a body of water an amount sufficient to inhibit growth or development of said algae, spores, barnacles or bacteria of a compound of the formula

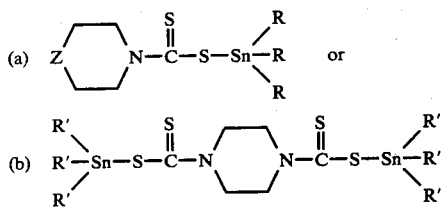

wherein R is an alkyl group of 2-4 carbon atoms, R' is an alkyl group of 1-4 carbons or phenyl, and Z is O or $CH_2$. Where said body of water is confined to a determined area, such as a fire pond, a cooling system or the like, I can be added to said water in an amount of from 1 to 100 ppm, and where specific surfaces are to be protected such as boats, ships, mooring birth etc., I is preferably used by means of a coating or paint which contains between 20 and 100 lbs. of I per 100 gallons (about 2–10% by weight) of said coating or paint. This level of I can be used in the customary paint formulations used for marine paint and causes no deterioration of said paint under normal storage conditions. When applied as coating or paint to the surface to be protected, most of such paint formulations containing up to 5% by weight of I, show no significant effect to the color of said paint. Paints stored for several months under standard storage conditions and containing up to 10% by weight of I retain their initial color, texture and viscosity.

The compounds of formula I (a) wherein the R substituents are the same or different alkyl groups, are made according to the procedure shown in British Pat. No. 841,151, using trialkyl stannic chloride. The compounds of I (b) are made in the same fashion but using piperazinyl-N-N'-bis(dithiocarbamate) and 2 molar equivalents of trialkyl or triphenyl tin chloride.

To illustrate the different use of the new additive, reference is made to the following examples which are not to be construed to limit this invention in any fashion.

EXAMPLE 1

To a commercial marine paint formulation containing 20.9% of an acrylic polyester resin combination, 18.9% of titanium dioxide pigment and 60.2% by weight of an aromatic hydrocarbon solvent is added 20–100 lbs. of the compound of structure I per 100 gal. of paint, and the additive is mixed into the paint until it is uniformly blended. Over the entire range, the formulations remain clear white and upon room temperature storage, substantially no changes are noticed in viscosity, texture or whiteness.

EXAMPLE 2

The compounds of formula I were placed in specified quantities in a circular plastic container whose open end was then covered with a membrane of known porosity. Complete units of this type were attached to three different locations on a raft:

(a) a well illuminated, aerated surface which favors plant settlement and growth,
(b) a poorly illuminated, deeper sited surface which favors bacterial growth and spore development,
(c) a location between (a) and (b), favoring both, bacterial and plant growth.

The raft is placed in an ocean bay and the containers are observed and compared with containers containing known anti-fouling compounds for several months of exposure to the natural environment. The control compound in this instance was an organo-arsenical currently used as a commercial, marine anti-fouling additive. Test compounds and control were used at levels of 0.3 g.

After 14 weeks, the compounds identified below showed the following results in comparison with three industry standards tested side-by-side with them. The comparison was made by visual inspection of the containers and is shown only as better, equal or worse than the standards.

| Compound | Type of I | R or R' | Z | Result |
|---|---|---|---|---|
| a) | a | n-butyl | O | better |
| b) | a | ethyl | $CH_2$ | equal |
| c) | a | n-propyl | $CH_2$ | better |
| d) | a | n-butyl | $CH_2$ | better |
| e) | b | methyl | — | worse |
| f) | b | phenyl | — | worse |
| g) | a | ethyl | O | worse |

EXAMPLE 3

A commercial boat bottom paint was divided into 2 samples for a yellowing test under normal storage conditions. One sample was kept as a control; to the other, the compound of formula Ia (Z=O; R=$nC_4H_9$) was added at a level of 80 lbs/100 gal. of paint (about 8% by weight). After storing both samples at room temperature for 1 month, 3-mil. drawdowns were prepared and the yellowing index was measured on both with a Hunter Color Difference meter. The unaltered paint drawdown showed an index of 4.6; the paint containing the new antifouling compound had an index of 5.4, proving that there is essentially no difference in color appearance between the samples.

EXAMPLE 4

(A) The compounds identified in Example 2 were also tested specifically for their antifungal activity in paint according to a standard test: Paint containing 0.5 lb./100 gal. (approx. 0.05% by weight) of the test compound was spread on a filter paper and from each sample, one was tested without leaching (UL) while another sample was placed under running water for a 24-hour leach (L). The paper samples were then placed in agar which was inoculated with a mixture of *A. niger* and *P. funiculosum*. The growth of the organisms was then recorded for each compound after three days and seven days and given a rating from a scale of 0–4 with 0 indicating no organism growth and 4 meaning normal growth. The results are shown in the table below.

(B) Some of the above paints were also exposed in a field test in Puerto Rico: A white paint formulation containing 0.4% by weight of the test compound was subjected to the effects of weather, molds and mildew. A scale of 0–10 was used to rate the paints with a reading of 7–10 indicating good to excellent resistance, 0–2 indicating no resistance to molds or mildew under natural environment after 7–8 months exposure. The results are also shown in the following table.

| Compound of Example 2 | L 3 | L 7 days | UL 3 | UL 7 days | Paint Rating |
|---|---|---|---|---|---|
| a | 0 | 4 | 0 | 4 | 7 |
| b | 0 | 0 | 0 | 1 | 7 |
| c | 0 | 4 | 0 | 4 | |
| d | 0 | 2 | 0 | 2 | 8 |
| e | 0 | 0 | 0 | 0 | 8 |
| f | 1 | 3 | 0 | 0 | 8 |

(C) In addition, it was determined that in standard MIC-tests (minimum inhibitory concentration), the compounds identified in Example 2 as (c) and (d) showed no fungal growth at 10 ppm or below and compounds (a), (b), (f) and (g) showed no growth at 100 ppm. or have an MIC of between 10 and 100.

While all the compounds of formula Ia and Ib show excellent antifouling activity when used in paint or other coatings according to a formulation such as shown in Example 1, they may also be used as a direct additive to standing or recirculating bodies of water, but obviously, greater dilution levels will be employed as indicated above. This use is of importance in cases where water is used for cooling purposes in confined areas such as cooling towers, particularly where salt water is used for that purpose. It is also useful in fresh water ponds used for fire protection or in ocean bays that do not have a continuous high exchange of water with adjacent bodies of water and are primarily used as protective harbors.

While the compounds of type I(a) are known, the compounds of types I(b) have heretofore not been described. These new compounds possess the above unique antifouling or aquatic pesticidal activities and they are easily prepared by simple condensations of the selected tin polyalkyl or polyphenyl and <0.5 molar equivalents of piperazinyl dithiocarbamate.

I claim:

1. A compound of the formula

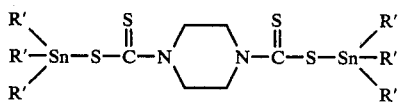

wherein each R' is an alkyl group of 1–4 carbon atoms or phenyl.

2. The compound of claim 1, wherein each R' is methyl.

3. The compound of claim 1, wherein each R' is phenyl.

* * * * *